Figures 1, 2, 3:
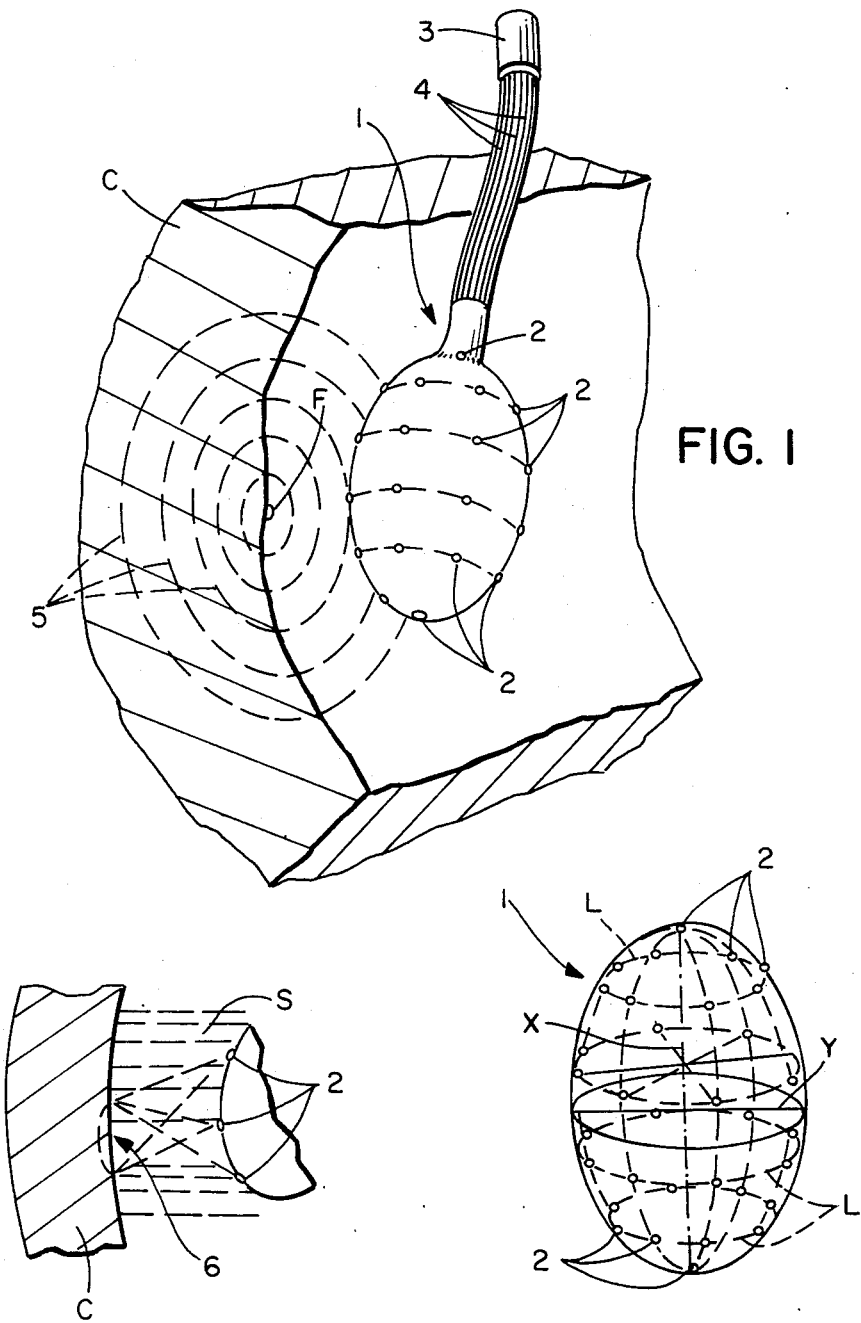

United States Patent [19]

Taccardi

[11] Patent Number: 4,649,924
[45] Date of Patent: Mar. 17, 1987

[54] METHOD FOR THE DETECTION OF INTRACARDIAC ELECTRICAL POTENTIAL FIELDS

[75] Inventor: Bruno Taccardi, Parma, Italy

[73] Assignee: Consiglio Nazionale Delle Ricerche, Rome, Italy

[21] Appl. No.: 752,903

[22] Filed: Jul. 8, 1985

[30] Foreign Application Priority Data

Aug. 14, 1984 [IT] Italy ............................. 53738/84[U]

[51] Int. Cl.$^4$ .............................................. A16N 5/04
[52] U.S. Cl. ................................. 128/642; 128/419 P; 128/786
[58] Field of Search ............... 128/639, 641, 642, 644, 128/772, 773, 774, 784, 785, 786, 419 P, 419 D

[56] References Cited

U.S. PATENT DOCUMENTS

| | | | |
|---|---|---|---|
| 3,326,207 | 6/1967 | Egan | 128/642 |
| 3,638,656 | 2/1972 | Grandjean et al. | 128/419 P |
| 4,198,963 | 4/1980 | Barkalow et al. | 128/419 D |
| 4,304,239 | 12/1981 | Perlin | 128/642 |
| 4,351,330 | 9/1982 | Scarberry | 128/786 |
| 4,401,127 | 8/1983 | Littleford | 128/419 P |
| 4,522,212 | 6/1985 | Gelinas et al. | 128/786 |

FOREIGN PATENT DOCUMENTS

| | | | |
|---|---|---|---|
| 2348241 | 9/1973 | Fed. Rep. of Germany | 128/644 |
| 0133400 | 1/1979 | Fed. Rep. of Germany | 128/786 |
| 8113428 | 12/1981 | PCT Int'l Appl. | 128/785 |

OTHER PUBLICATIONS

Berens et al, "New Stable Temporary Atrial Pacing Loop", Sep. 1974, American Journal of Cardiology (vol. 34), pp. 325-332.

Primary Examiner—Edward M. Coven
Attorney, Agent, or Firm—Lahive & Cockfield

[57] ABSTRACT

A catheter method for detecting intracardiac electrical potential fields makes use of a catheter provided with sensor electrodes which are connected through conductor wires to a signal receiver and processor. The catheter is inserted into the right or left ventricle through a hole formed in a vein or artery in a catheterization theatre, or during open thorax surgery, while normal cardiac function is maintained. The catheter has a distal end portion which may be inflatable, the size and shape of this end portion being such that the sensor electrodes are spaced substantially from the wall of the cardiac chamber in use of the catheter.

9 Claims, 4 Drawing Figures

METHOD FOR THE DETECTION OF INTRACARDIAC ELECTRICAL POTENTIAL FIELDS

The present invention relates to a method for the detection of intracardiac electrical potential fields, by means of a catheter having a distal end portion provided with a series of sensor electrodes distributed over its surface and connected to insulated electrical conductors intended for connection to means for receiving and processing the signals picked up by the sensor electrodes.

A method of the type specified above is described in the Article "Endocardial mapping by simultaneous recording of endocardial electrograms during cardiac surgery for ventricular aneurysm" by Jacques M. T. de Bakker et al, JACC Vol. 2, No. 5, November 1983, pages 947–953. This known method is used to record a plurality of endocardial electrograms simultaneously during cardiac surgery on patients subject to aneurismectomy and/or endocardial resection. The object of endocardial resection is to prevent the occurrence of serious ventricular tachycardia, this often being present in these subjects and not always being correctable by medical care. The distal end portion of the said catheter is constituted by an inflatable balloon carrying the aforementioned sensor electrodes. In use, the balloon, after having been inserted into a ventricle, is inflated so as to bring the sensor electrodes into contact with the wall of the cardiac chamber. Obviously this operation is carried out after extracorporeal circulation has been started so as to empty the heart of blood. After the beginning of tachycardia, which is induced by programmed stimulation should it not be present naturally at the time of the operation, the signals picked up by the sensor electrodes are stored and analysed so as to determine the electrode which was activated first. The operation takes between 2 and 5 minutes.

Although the method carried out with the catheter described above has advantages over methods previously used for the detection of the point of origin of potentially lethal ventricular arrhythmia, it has, however, the disadvantage, as mentioned above, of being useable only during surgery of the type with extracorporeal circulation, with the heart empty. Use during cardiac catheterization is excluded. Furthermore, when the heart is open, it may not be possible to induce tachycardia or its characteristics may be changed.

The object of the present invention is to provide a method of the type specified at the beginning of the present description which allows the point of origin of ventricular arrhythmia to be detected during normal cardiac function, for example in a catheterization theatre or during surgery, without extracorporeal circulation, and which requires a single cardiac beat to provide the required result.

In order to achieve this object, the invention provides a new method for detecting intracardiac electrical potential fields of the type specified at the beginning of the present description, the main characteristic of which lies in the fact that the method includes the steps of introducing the distal end portion of the catheter into one of the ventricles, with the heart closed, while maintaining normal cardiac function, and effecting the detection with the sensor electrodes substantially spaced from the wall of the cardiac chamber.

A further object of the present invention is that of providing a catheter which allows the said method to be carried out.

This object is achieved by virtue of the fact that the said distal end portion is so shaped that when it is inserted in a cardiac chamber, the sensor electrodes are generally spaced substantially from the wall of the cardiac chamber.

Preferably the said distal end portion has a volume of between 1/5th and 1/10th of the volume of the cardiac chamber, whereby the catheter according to the invention may be used, as mentioned above, during normal functioning of the heart. This is not, however, possible with the solution used in the known method mentioned previously which, in the operative condition, assumes a volume equal to that of the cardiac chamber. In the case of the present invention, the blood present in the cardiac chamber acts as a conductive medium and allows the electrodes distributed over the distal end portion of the catheter to detect the electrical potential present on the surface of the end portion itself. At any instant after the start of tachycardia, possibly caused by programmed cardiac stimulation, the sensor electrodes signal the instantaneous electrical potential field relative to the cardiac beat. The potential field has a minimum in correspondence with the electrode which faces the zone of origin of the tachycardia.

In a preferred embodiment, the said distal end portion of the catheter is substantially ellipsoidal in shape. The sensor electrodes are distributed on a series of circumferences lying in planes spaced from each other and perpendicular to the major axis of the said ellipsoidal end portion. At least two further sensor electrodes are also provided adjacent the ends of the major axis. There may for example be four of the said circumferences and eight sensor electrodes equiangularly spaced from each other may be arranged on each of these circumferences. In one embodiment, the major axis of the ellipsoidal end portion of the catheter is about 40 mm and the minor axis is about 20 mm.

Preferably the said ellipsoidal end portion is constituted by an inflatable body. It is, however, possible to make the end portion of the catheter in the form of a rigid body.

The catheter according to the invention has the basic advantage of being usable during normal functioning of the heart.

Figure 4:
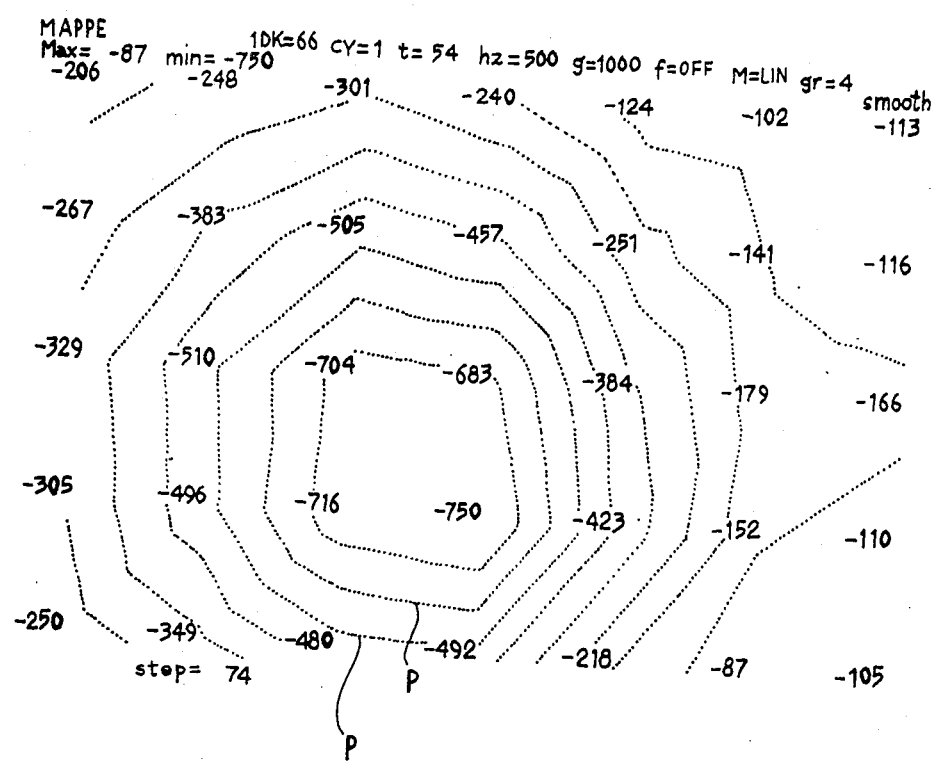

Further characteristics and advantages of the method and of the catheter according to the invention will become apparent from the description which follows with reference to the appended drawings, provided purely by way of non-limiting example, in which:

FIG. 1 is a schematic perspective view of part of a catheter according to the present invention illustrated adjacent a portion of a cardiac wall, FIG. 2 is a schematic view illustrating the principle of operation of the catheter according to the invention, FIG. 3 is a schematic diagram illustrating the distribution of the sensor electrodes over the surface of the distal end portion of the catheter of FIG. 1, and FIG. 4 illustrates an example of a map of electrical potential on the surface of the distal end portion of the catheter which can be obtained by means of the catheter according to the invention during a closed heart operation.

In the example illustrated in FIG. 1, the catheter according to the invention has a distal end portion 1 constituted by an inflatable body which, in the expanded condition illustrated in FIG. 1, assumes an ellipsoidal shape. The structure of this body and the material forming it may, for example, be of the type illustrated for the known catheter described in the technical article mentioned in the introduction to the present description.

A series of sensor electrodes 2 is distributed over the outer surface of the body constituting the end portion 1 of the catheter. FIG. 3 illustrates one possible disposition of these sensor electrodes. In this example, the electrodes are disposed on four imaginary circumferences L lying in four planes spaced from each other and perpendicular to the major axis X of the ellipsoidal end portion 1. Eight sensor electrodes 2 are equiangularly spaced from each other on each circumference L. Two further sensor electrodes 2 are also provided adjacent the ends of the major axis X.

In one practical embodiment, the length of the major axis X was about 40 mm and that of the minor axis Y (see FIG. 3) was about 18 mm, a size suitable for an adult heart.

For childrens' hearts the dimensions are reduced in proportion. The sensor electrodes 2 are constituted by silver plates of, for example, flat circular shape of about 0.5 mm diameter. In the embodiment illustrated, the catheter also has a tube 3 terminating in the distal end portion 1 and containing a series of electrical conductor wires 4, preferably of silver, insulated from each other and connected to the respective sensor electrodes 2. The conductor wires 4 are not illustrated for reasons of clarity in FIG. 3.

Obviously, the conformation and disposition of the sensor electrodes 2 could be different from that explained above purely by way of example.

The electrical conductor wires 4 are intended for connection at their opposite ends from the sensor electrodes 2 to means for receiving and processing the signals picked up by the sensor electrodes. These means may be constituted by a conventional instrument for recording cardiac maps such as for example the apparatus marketed by the Italian company Battaglia Rangoni di Casalecchio di Reno, under the name "Cardimap 2".

In use, the catheter described above may be introduced without surgery in a catheterization theatre and in this case the introduction into the right ventricle is carried out through a small hole formed in a peripheral vein; the introduction into the left ventricle is effected through a peripheral artery. During surgery, the introduction into the right ventricle is effected through a hole formed in the superior vena cava or in the right auricle. The introduction into the left ventricle is effected through a pulmonary vein or the left auricle or possibly the aorta. During the operation, the catheter is introduced with the thorax open but the heart closed before the initiation of extracorporeal circulation. In the example described above, the end portion 1 of the catheter is obviously introduced in the uninflated condition and is inflated after the introduction by the immission of oil or a physiological solution. After the start of tachycardia, which as already mentioned may be caused by the known method of programmed cardiac stimulation, should tachycardia not be present naturally at the time of the operation, the instrument connected by the electrical conductor wires 4 to the sensor electrodes 2 records a series of maps relative to the cardiac beat. These maps constantly show a minimum potential located at the point on the surface of the end portion 1 of the catheter which faces the zone of origin of the tachycardia. Thus the endocardial region from which arrhythmia starts is easily identifiable. One example of a map which can be obtained by means of a catheter of the type described above is illustrated in FIG. 4.

This map shows a series of equi-potential lines P distinguished by a series of negative potential values. The zone corresponding to the minimum potential, that is the negative potential having the highest absolute value, is that which faces the seat or focus of the tachycardia.

The reason for this phenomenon is explained with reference to FIGS. 1 and 2. In these Figures, reference C indicates the wall of the cardiac chamber while reference S indicates the blood which fills the cardiac chamber. After tachycardia has started, an excitation wave-front propagates within the thickness of the cardiac wall starting from the focus F in accordance with the wave lines 5, with a velocity of the order of 1 m/sec. If at any given instant the wave-front which is propagated covers the surface portion indicated 6 in FIG. 2, the sensor electrode 2 which "views" the surface portion 6 with the maximum viewing angle (the central electrode in FIG. 2) is that which registers the highest absolute value of negative potential. In the majority of cases, the focus F (FIG. 1) is located on the endocardial surface (portion 6 of FIG. 2).

In rarer cases the focus F is located within the thickness of the ventricular wall. In these cases, the situation described in FIG. 2 is reproduced immediately the excitation wave-front reaches the ventricular cavity. Again in these cases the maps show a potential minimum located at the point of the surface of the end portion 1 of the catheter which faces the zone of origin of the tachycardia.

As already stated, the blood S acts as a conductive medium and allows the sensor electrodes 2 to detect the potential field generated by the excitation wave-front which is propagated through the cardiac wall. After a single cardiac beat it is possible to obtain immediately a map of the type illustrated in FIG. 4 so that the focus of the tachycardia can be identified promptly. It is thus possible to identify this in a very short time without disturbing the normal cardiac function. By virtue of this rapidity, the method of the invention may be used even with tachycardia of very short duration. The method also lends itself to the study of other rhythm and conduction disturbances, for example extrasystoles, Wolff-Parkinson White disease, and fascicular blocks.

In one variant, the distal end portion 1 of the catheter is in the form of a rigid body.

I claim:

1. A method for detecting the site of origin of ventricular arrhythmias during a single heartbeat, comprising the steps of:

providing a catheter having a distal end portion with a continuous outer surface on which a series of sensor electrodes are distributed, and a series of insulated electrical conductors located within said catheter and connecting said sensor electrodes to means for receiving and processing signals picked up by said sensor electrodes, said distal end portion on which the sensor electrodes are located having a volume less than the volume of a cardiac chamber into which said distal end portion is to be inserted, introducing said distal end portion into the cardiac chamber with the heart closed, while maintaining the outer surface of said distal end portion spaced apart from the wall of said cardiac chamber, so that normal cardiac functions can be maintained, and detecting at least once during a single heartbeat the electric potentials picked up by said sensor electrodes on said outer surface, identifying thereby the site of origin of the arrhythmia as the portion of the heart closest to the electrode which has detected the most negative value of electric potential.

2. A method according to claim 1 wherein the distal end portion of the catheter is introduced into the cardiac chamber through the circulatory system, with the thorax closed.

3. A method according to claim 1 wherein the distal end portion of the catheter is introduced in the cardiac chamber through the circulatory system, with the thorax open.

4. A method according to claim 1 wherein said distal end portion of the catheter on which the sensor electrodes are loaded has a volume of between 1/5th and 1/10th of the volume of the cardiac chamber.

5. A method of according to claim 1 wherein said distal end portion of the catheter on which the sensor electrodes are located has an ellipsoidal shape.

6. A method according to claim 5 wherein said ellipsoidal end portion of the catheter has a major axis of about 40 mm and minor axis of about 18 mm.

7. A method according to claim 5 wherein the sensor electrodes are distributed on a series of circumferences lying in planes spaced from each other and perpendicular to the major axis of said ellipsoidal end portion, and wherein at least two further sensor electrodes are provided, each of said further sensor electrodes being adjacent to a respective ends of said major axis.

8. A method according to claim 7 wherein there are four of said circumferences, and eight of said sensor electrodes are equiangularly spaced apart on each of said circumferences.

9. A method according to claim 1, wherein said distal end portion of the catheter on which the sensor electrodes are located is an inflatable body.

* * * * *